US00PP14836P2

(12) United States Plant Patent
Heims

(10) Patent No.: US PP14,836 P2
(45) Date of Patent: May 25, 2004

(54) HEUCHERA PLANT NAMED 'OBSIDIAN'

(50) Latin Name: *Heuchera hybrid*
Varietal Denomination: Obsidian

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 33 days.

(21) Appl. No.: 10/452,950

(22) Filed: Jun. 2, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H. Para
(74) *Attorney, Agent, or Firm*—Klarquist Sparkman, LLP

(57) ABSTRACT

A new and distinct hybrid of Heuchera plant characterized by dark, almost black leaves and a compact habit.

1 Drawing Sheet

Botanical classification: *Heuchera hybrid.*
Variety denomination: 'Obsidian'.

The present invention relates to a new and distinct cultivar of *Heuchera hybrid* and given the cultivar name of 'Obsidian'. Heuchera is in the family Saxifragaceae. Heuchera 'Obsidian' originated from a cross between unknown parents. This new Heuchera was selected from seedlings grown from select interspecfic hybrids that were open pollinated in the field in Canby, Oreg. Given its characteristics we know that *Heuchera americana* is in its parentage.

This new and unique Heuchera is distinguished by:

1. Almost black colored leaves.
2. Medium leaf size.
3. Compact habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
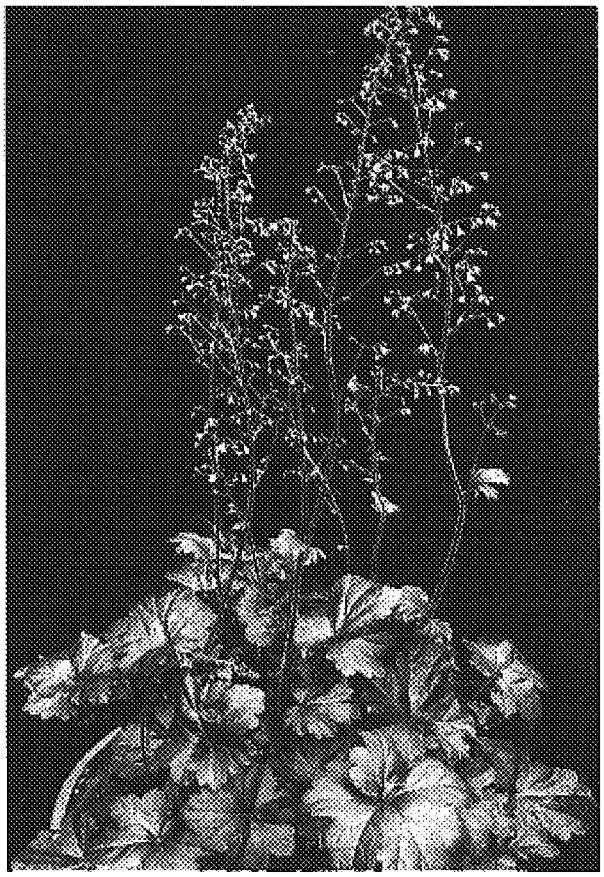
FIG. 1 shows Heuchera 'Obsidian' growing in a two gallon pot in July in Canby, Oreg.
Figure 2:
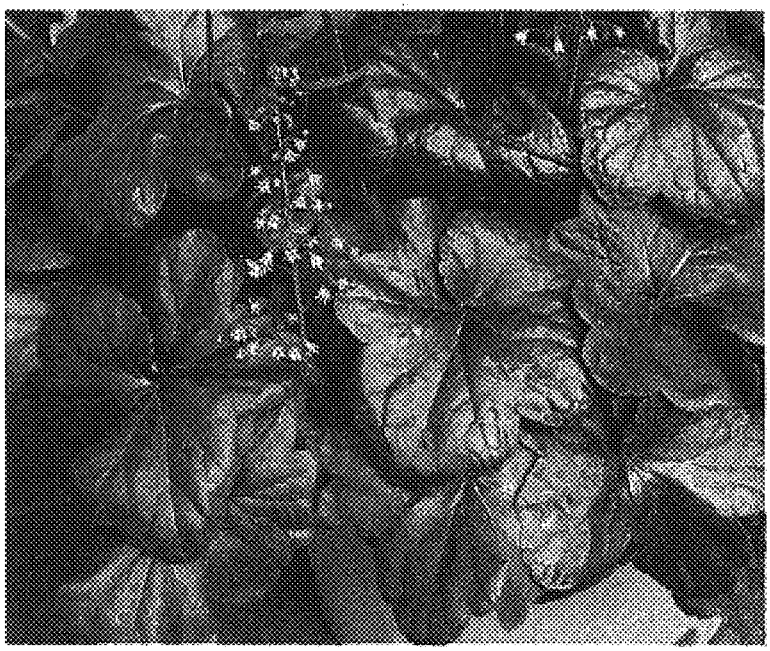
FIG. 2 shows a close up Heuchera 'Obsidian' growing in a pot in a shaded greenhouse in spring.

The following is a detailed description of the new Heuchera hybrid based on observations of one and a half year old specimen grown in a two gallon container in a greenhouse in Canby, Oreg. The color descriptions are all based on The Royal Horticultural Society Colour Chart.

Botanical Classication: *Heuchera hybrid.*
Variety denomination: 'Obsidian'.

Plant:
- *Form.*—Basal rosette, herbaceous perennial.
- *Hardiness.*—USDA Zone 4 to 9.
- *Size.*—23 cm tall and 35 cm wide.
- *Habit.*—Compact, rounded.

Leaf:
- *Type.*—Simple.
- *Arrangement.*—Rosette.
- *Shape* — Orbicular to slightly ovate.
- *Lobing/division* .—7 shallow rounded lobes, with 1 to 2 shallow secondary lobes.
- *Venation.*—Palmate.
- *Margins.*—Widely crenate.
- *Apex.*—Mucronulate to obtuse.
- *Base.*—Cordate, lobes overlapping.
- *Blade size.*—9.5 to 14 cm long and 9 to 13 cm wide.
- *Vestiture.*—Sparsely puberulous.
- *Aspect.*—Matte.
- *Texture.*—Thin, leathery.
- *Petiole length.*—17 to 18 cm.
- *Petiole texture.*—Glandular puberulent.
- *Petiole color.*—Greyed Orange 177A and Greyed Purple 183A.
- *Leaf color.*—Topside — In spring Greyed Purple 187A but blacker. In summer the color is closest to Black 202A. If grown in shade the color is more olive, Brown 200A over Green 147A. Bottomside — In between Greyed Purple 187A and Red Purple 70A.

Inflorescence:
- *Type.*—Thyrse.
- *Number of flowers.*—about 100 per thyrse.
- *Peduncle.*—With 1 or 2 very small (0.5 cm) bracts per scape, unbranched. Height — 34 to 44 cm. Diameter — 0.3 cm. Color — Greyed Orange 177A. Texture — Glandular puberulent.
- *Pedicel.*—Length — 0.2 to 0.5 cm. Texture — Glandular puberulent. Color — Greyed Orange 177A
- *Bloom period.*—May through August in Canby, Oreg.

Flower bud:
- *Size.*—0.2 cm wide.
- *Description.*—Glandular puberulent, ovoid.
- *Color.*—Greyed Purple 186A with Greyed Yellow 160A at tip.

Flower:
- *Type.*—Perfect, zygomorphic.
- *Shape.*—Insignificant, campanulate.

*Size.*—0.4 cm long and 0.3 cm wide.

*Petal count.*—5, inconspicuous.

*Petal color.*—White 155D with pink tips, Red Purple 62B.

*Petal shape.*—Elliptic with a clawed base.

*Petal size.*—About 0.3 cm long.

*Calyx.*—Divided ⅓ way to the base, with glandular hairs, urceolate.

*Calyx color.* —Red brown, Greyed Orange 174A with lime green tips and edges, Yellow Green 154C.

*Sepal number.*—5 lobes.

*Sepal size.*—0.2 cm long and 0.15 cm wide.

*Stamen number.*—5.

*Pistil color.*—Yellow Green 154D.

*Pollen color.*—No pollen, male sterile.

*Fragrance.*—None.

*Lastingness.*—Each thryse blooms for about 2 weeks on the plant.

Fruit:

*Type.*—Two-beaked ovoid capsule.

*Fertility.*—Low.

*Color.*—Tan. RHS 160C Greyed-Yellow to 199C Grey-Brown.

Seed:

*Shape.*—Linear.

*Size.*—2 mm. long.

*Color.*—Black RHS 202A.

Disease tolerance: Excellent disease resistance to powdery mildew, the common problem of Heuchera.

COMPARISON TO SIMILAR HEUCHERA

Compared to Heuchera 'Black Beauty' (U.S. Pat. No. 13,288), Heuchera 'Obsidian' has darker, rounder leaves that don't undulate and a matte aspect rather than glossy.

Compared to *Heuchera americana* 'Palace Purple', an unpatented plant, Heuchera 'Obsidian' has darker, rounder, less crinkled leaves and a neater, rounder habit.

Compared to Heuchera 'Midnight Claret' or 'Midnight Burgundy' (both unpatented plants) this new cultivar is larger, with rounder leaves that are unmarked by any silvering.

I claim:

1. A new and distinct hybrid of Heuchera plant substantially as shown and described, characterized by dark, almost black leaves and a compact habit.

* * * * *